United States Patent
Furudate (10) Patent No.: US 9,110,144 B2
(45) Date of Patent: Aug. 18, 2015

(54) MAGNETIC RESONANCE IMAGING APPARATUS AND MAGNETIC RESONANCE METHOD

(75) Inventor: Naoyuki Furudate, Otawara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 701 days.

(21) Appl. No.: 13/438,259

(22) Filed: Apr. 3, 2012

(65) Prior Publication Data

US 2012/0256627 A1 Oct. 11, 2012

(30) Foreign Application Priority Data

Apr. 6, 2011 (JP) .................................. 2011-084132
Mar. 2, 2012 (JP) .................................. 2012-047434

(51) Int. Cl.
*G01V 3/00* (2006.01)
*G01R 33/54* (2006.01)
*A61B 5/055* (2006.01)
*G01R 33/56* (2006.01)
*G01R 33/563* (2006.01)

(52) U.S. Cl.
CPC ............ *G01R 33/543* (2013.01); *G01R 33/546* (2013.01); *A61B 5/055* (2013.01); *G01R 33/5602* (2013.01); *G01R 33/5608* (2013.01); *G01R 33/56333* (2013.01)

(58) Field of Classification Search
CPC ..................................................... G01R 33/546
USPC .......................... 324/309, 307, 306, 312, 314
See application file for complete search history.

(56) References Cited

U.S. PATENT DOCUMENTS 5,519,320 A * 5/1996 Kanayama et al. ........... 324/309
5,777,473 A * 7/1998 Takai et al. .................... 324/309
7,808,239 B2 * 10/2010 Miyazaki ...................... 324/309

FOREIGN PATENT DOCUMENTS

CN 101441254 A 5/2009
JP 2004-357834 12/2004

OTHER PUBLICATIONS

Office Action issued Jan. 17, 2014, in CN Patent Application No. 201210099870.X.

* cited by examiner

*Primary Examiner* — Louis Arana
(74) *Attorney, Agent, or Firm* — Oblon, McClelland, Maier & Neustadt, L.L.P.

(57) ABSTRACT

According to one embodiment, a magnetic resonance imaging apparatus includes an imaging condition setting unit, a verification image generating unit and an imaging unit. The imaging condition setting unit is configured to set an imaging condition for applying radio frequency pre-pulses to adjust a contrast. The radio frequency pre-pulses includes a region selective radio frequency pulse. The verification image generating unit is configured to generate and display an image for verifying the contrast based on application conditions including an application region and an application number of the radio frequency pre-pulses. The imaging unit is configured to perform magnetic resonance imaging according to the imaging condition.

15 Claims, 8 Drawing Sheets

MAGNETIC RESONANCE IMAGING APPARATUS AND MAGNETIC RESONANCE METHOD

CROSS REFERENCES

This application is based upon and claims the benefit of priority from Japanese Patent Application No. 2011-084132, filed Apr. 6, 2011 and Japanese Patent Application No. 2012-47434, filed Mar. 2, 2012; the entire contents of which are incorporated herein by reference.

FIELD

Embodiments described herein relate generally to a MRI (magnetic resonance imaging) apparatus and a magnetic resonance imaging method.

BACKGROUND

MRI is an imaging method which excites nuclear spin of an object set in a static magnetic field with a RF (radio frequency) signal having the Larmor frequency magnetically and reconstructs an image based on MR (magnetic resonance) signals generated due to the excitation.

In MRI, various pre-pulses are applied as RF pulses prior to data acquisition in order to obtain an image having a desired contrast. For example, in MRA (magnetic resonance angiography) method to perform imaging of a blood vessel, a spin labeling pulse (also referred to a tagging pulse) is applied in order to obtain a contrast difference between a blood flow and a background tissue.

The spin labeling pulse is a pre-pulse for tagging spins included in fluid such as blood or CSF (cerebrospinal fluid) which flows into an imaging section. Especially, a spin labeling pulse for spin labeling of blood is called an ASL (Arterial spin labeling) pulse.

A t-SLIP (TIME-SLIP: time-Spatial Labeling Inversion Pulse) is known as a representative spin labeling pulse used in non-contrast-enhanced MRA. The t-SLIP includes a region non-selective IR (inversion recovery) pulse and a region selective IR pulse. It is possible to set a region selective IR pulse arbitrarily independent of an imaging region. Therefore, when NMR signals are suppressed by a region non-selective IR pulse while a labeling region is labeled by a region selective IR pulse so that NMR signals from blood in a specific region is enhanced, blood flowing out of the labeling region after a TI (inversion time) can be selectively depicted as a high signal part.

Note that, a region non-selective IR pulse can be switched between ON/OFF. When a region non-selective IR pulse is set to OFF, signals from blood included in a labeling region are suppressed by application of a region selective IR pulse. Therefore, blood flowing out of the labeling region after a TI is depicted as a low signal region.

In addition to the t-SLIP as mentioned above, a RF pulse such as a saturation pulse is used for adjusting a contrast. A presaturation (Presat) pulse applied as a RF pre-pulse is a pre-pulse for suppressing signals from a desired matter by saturating spins of the desired matter.

RF pre-pulses, including a t-SLIP and a Presat pulse, each applied for adjusting a contrast can be combined mutually. That is, MR images having various contrasts can be acquired by applying plural similar or dissimilar region selective RF pre-pulses or region non-selective RF pre-pulses prior to data acquisition.

When application of a single RF pre-pulse is set at the time of setting imaging conditions, an intended contrast can be grasped easily. That is, at the time of setting imaging conditions, an operator can easily grasp that an image having what contrast is acquired.

However, when application of plural RF pre-pulses including a region selective RF pre-pulse is set, there is a possibility that the intended contrast cannot be grasped easily. For example, when application regions of plural region selective RF pre-pulses are different and there is an overlap section between the application regions, spins included in the overlap section receive influences of the respective region selective RF pre-pulses. In addition, when a 180-degree region non-selective IR pulse is applied, the longitudinal magnetization of spins is inverted by 180 degrees and sections showing high signals and low signals are inverted.

Consequently, there is a possibility that an operator cannot easily grasp contrasts possible in respective sections of an imaging region.

An object of the present invention is to provide a magnetic resonance imaging apparatus and a magnetic resonance imaging method which make it possible to easily grasp an estimated contrast at the time of setting imaging conditions in case of imaging with applying a region selective pulse as a RF pulse for adjusting a contrast.

DETAILED DESCRIPTION

In general, according to one embodiment, a magnetic resonance imaging apparatus includes an imaging condition setting unit, a verification image generating unit and an imaging unit. The imaging condition setting unit is configured to set an imaging condition for applying radio frequency pre-pulses to adjust a contrast. The radio frequency pre-pulses include a region selective radio frequency pulse. The verification image generating unit is configured to generate and display an image for verifying the contrast based on application conditions including an application region and an application number of the radio frequency pre-pulses. The imaging unit is configured to perform magnetic resonance imaging according to the imaging condition.

Further, according to another embodiment, a magnetic resonance imaging method includes setting an imaging condition for applying radio frequency pre-pulses, including a region selective radio frequency pulse, to adjust a contrast; generating and displaying an image for verifying the contrast based on application conditions including an application region and an application number of the radio frequency pre-pulses; and performing magnetic resonance imaging according to the imaging condition.

A magnetic resonance imaging apparatus and a magnetic resonance imaging method according to embodiments of the present invention will be described with reference to the accompanying drawings.

Figure 1:
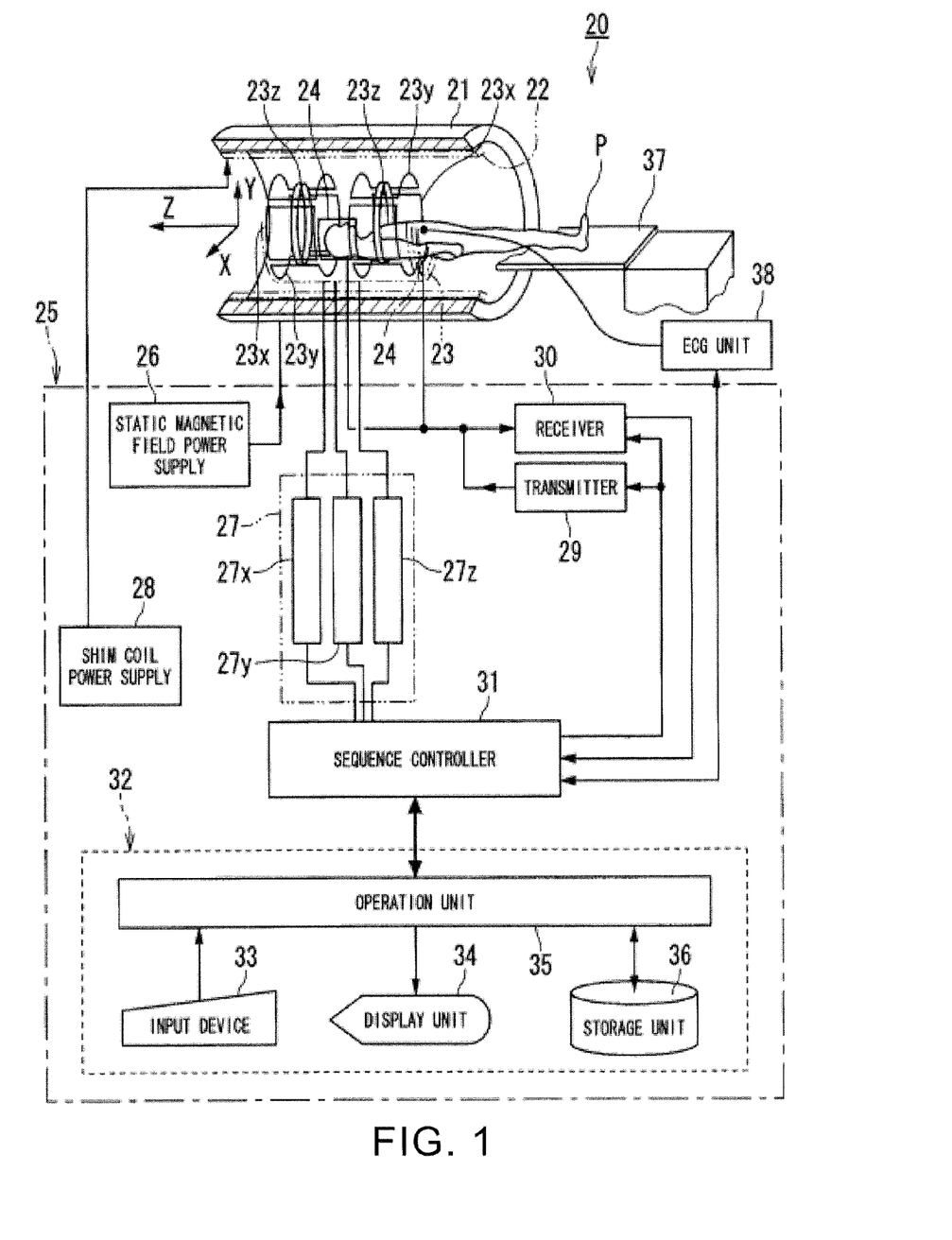
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 has a function to transmit a RF signal given from the transmitter 29 to the object P. The reception RF coil 24 has a function to receive a MR signal generated due to a nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to store sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27.

The sequence controller 31 is also configured to give raw data to the computer 32. The raw data is complex data obtained through the detection of a MR signal and A/D (analog to digital) conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In addition, an ECG unit 38 for acquiring an ECG (electro cardiogram) signal of the object P is provided with the magnetic resonance imaging apparatus 20. The ECG signal detected by the ECG unit 38 is output to the computer 32 through the sequence controller 31.

Note that, a PPG (peripheral pulse gating) signal representing a beat as pulse wave information may be acquired instead of an ECG signal representing a beat as heart rate information. A PPG signal is acquired by detecting a pulse wave of e.g. tip of a finger as an optical signal. When a PPG signal is acquired, a PPG signal detection unit is provided with the magnetic resonance imaging apparatus 20. Hereinafter, a case of acquiring an ECG signal will be described.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Figure 2:
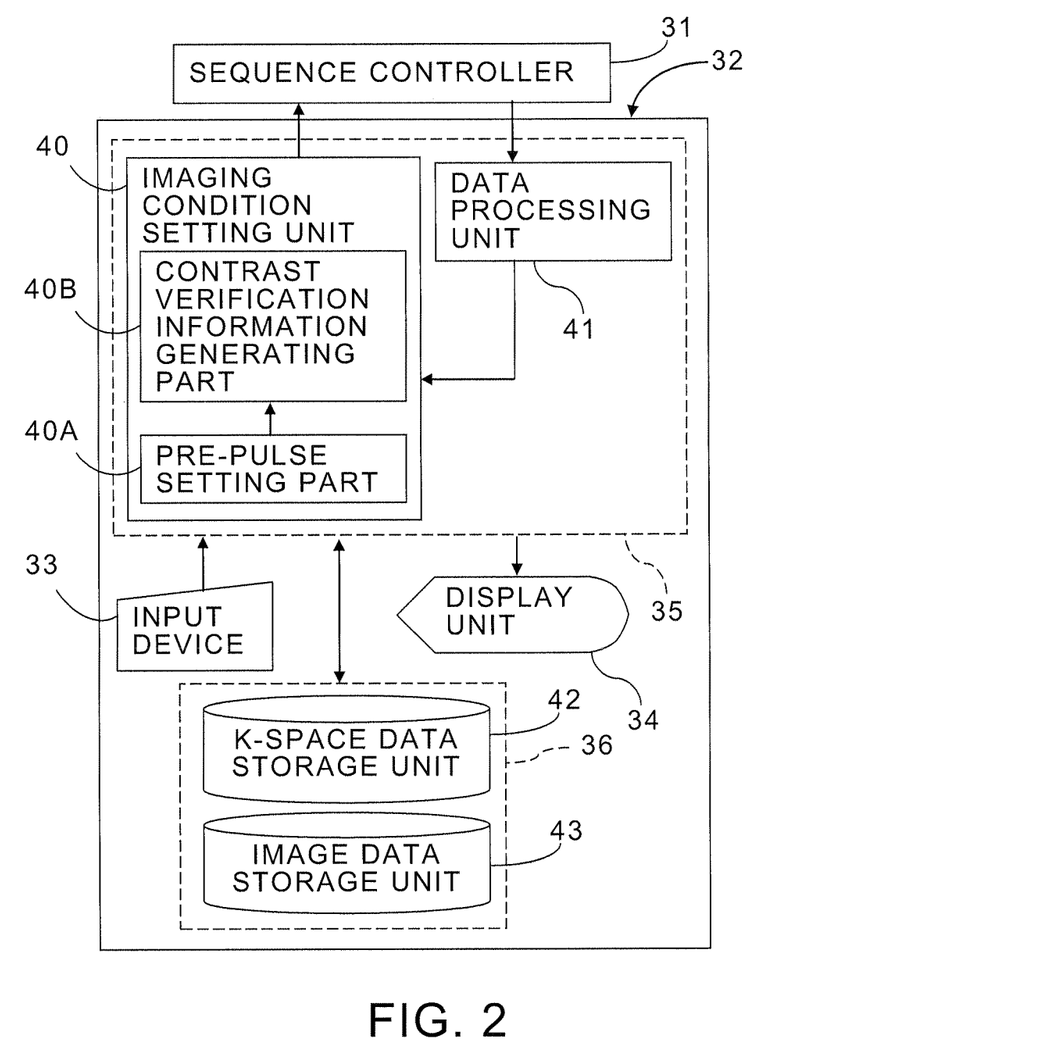
FIG. 2 is a functional block diagram of the computer shown in FIG. 1.

FIG. 2 is a functional block diagram of the computer 32 shown in FIG. 1.

The operation unit 35 of the computer 32 functions as an imaging condition setting unit 40 and a data processing unit 41 by executing a program stored in the storage unit 36. The imaging condition setting unit 40 has a pre-pulse setting part 40A and a contrast verification information generating part 40B. Further, the storage unit 36 functions as a k-space data storage unit 42 and an image data storage unit 43.

The imaging condition setting unit 40 has a function to set imaging conditions including a pulse sequence in accordance with instruction information from the input device 33 and output the set imaging conditions to the sequence controller 31. Especially, the imaging condition setting unit 40 has a function to set imaging conditions for applying RF pre-pulses, including at least one region selective RF pulse, to adjust contrast. For that reason, the imaging condition setting unit 40 is configured to display a setting screen of imaging conditions on the display unit 34 and set imaging conditions in accordance with the information input from the input device 33 with referring to the setting screen of the imaging conditions.

For example, in case of imaging fluid such as blood flow or CSF, a 3D (three dimensional) SSFP (steady state free precession) sequence or a 3D FASE (fast asymmetric spin echo or fast advanced spin echo) sequence for acquiring NMR data from a spatial area by a 3D scan is set as an imaging condition.

In addition, in case of imaging an object having periodicity such as blood flow by MRA, a delay time from a reference wave such as a R wave to a data acquisition time and the like are set as imaging conditions so that NMR data is acquired at a predetermined cardiac time phase in synchronized with a synchronizing signal such as an ECG signal.

The pre-pulse setting part 40A has a function to set RF pre-pulses to be applied in order to obtain a desired contrast as imaging conditions. The RF pre-pulses for adjusting contrasts include an IR pulse and a Presat pulse. The IR pulse is a pulse to invert a longitudinal magnetization vector by 180 degrees. The Presat pulse is a pulse to lay a longitudinal magnetization vector by 90 degrees to saturate spins.

Further, the RF pre-pulses include a region selective RF pre-pulse to which a spatial application region can be set and a region non-selective RF pre-pulse to which an application region cannot be set. When a region selective RF pre-pulse is applied, fluid such as blood flow included in an application region can be labeled (tagged). Therefore, after application of a region selective RF pre-pulse, it becomes possible to selectively depict fluid flowing out from the application region of the region selective RF pre-pulse to outside or flowing into the application region from outside of the application region.

The pre-pulse setting part 40A can set application conditions of RF pre-pulses as imaging conditions so as to apply a desired number of a same kind or different kinds of RF pre-pulses at desired timings. Especially, pulses derived by combining a region selective IR pulse with a non-region selective IR pulse which can be switched between ON and OFF are referred to as a t-SLIP. Then, condition parameters for a t-SLIP can be set so that a region selective IR pulse is applied plural times in a same desired region or different desired regions in order to obtain a desired contrast. Further, a RF pre-pulse for labeling arteries to depict the arteries selectively is referred to as an ASL pulse. In case of labeling fluid such as blood or CSF, at least one of RF pre-pulses is set to a labeling pulse, such as a region selective IR pulse or a region selective pre-saturation pulse, for labeling the fluid flowing in an object P.

The contrast verification information generating part 40B has a function to generate image information for visually verifying an image contrast obtained by RF pre-pulses set in the pre-pulse setting part 40A by an operator and a function to display the generated image information as contrast verification information on a setting screen of imaging conditions.

More specifically, the contrast verification information generating part 40B is configured to generate and display an image for verifying contrast based on application conditions, including at least application regions and the number of applications, of RF pre-pulses. In addition, an image showing influence of T1 relaxation according to respective application timings of RF pre-pulses may be generated as contrast verification information based on the application timings, as needed. Further, an image showing a flow of fluid with an estimated contrast may be generated as contrast verification information.

The data processing unit 41 has a function to arrange NMR signals obtained from the sequence controller 31 as k-space data in k-space formed in the k-space data storage unit 42, a function to reconstruct image data by reading k-space data from the k-space data storage unit 42 and performing image reconstruction processing including FT (Fourier transform) of the k-space data, a function to write image data into the image data storage unit 43 and a function to display image data read from the image data storage unit 43 on the display unit 34 with required image processing.

MIP (Maximum Intensity Projection) to display 3D image data as 2D (two dimensional) image data and subtraction processing between image data to selectively depict a target artery are examples of image processing.

Frames of locator image data generated in the data processing unit 41 are used for setting imaging conditions including an imaging region and application regions of RF pre-pulses in the imaging condition setting unit 40. In addition, desired frames of image data such as frames of locator image data generated in the data processing unit 41 can be used as data for generating image information as contrast verification information in the contrast verification information generating part 40B, as needed. For that purpose, the data processing unit 41 is configured to supply necessary frames of image data to the contrast verification information generating part 40B in response to requirement from the contrast verification information generating part 40B.

Next, operation and action of the magnetic resonance imaging apparatus 20 will be described.

Figure 3:
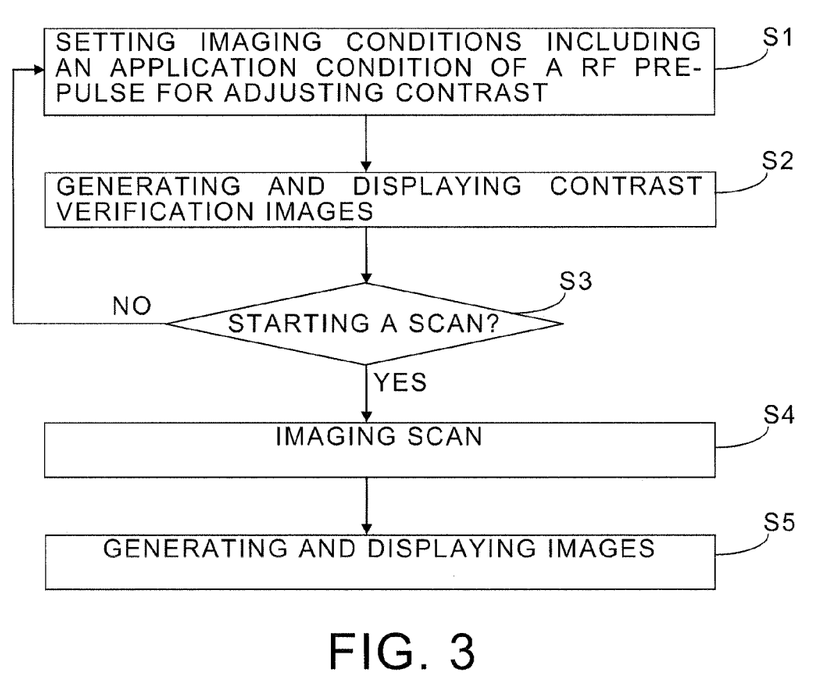
FIG. 3 is a flow chart to show a flow in performing imaging by setting image conditions with application of RF pre-pulses for obtaining a desired contrast by the magnetic resonance imaging apparatus shown in FIG. 1.

FIG. 3 is a flow chart to show a flow in performing imaging by setting image conditions with application of RF pre-pulses for obtaining a desired contrast by the magnetic resonance imaging apparatus 20 shown in FIG. 1.

An object P is set in advance on the bed 37 and a static magnetic field is generated in an imaging region of the static magnetic field magnet 21 (super conductive magnet) excited by the static magnetic field power supply 26. Then, the shim coil power supply 28 supplies current to the shim coil 22 so that the static magnetic field generated in the imaging region becomes uniform.

Furthermore, reference image data such as three orthogonal cross sections image data and locator image data to be required for setting image conditions including an imaging region are acquired in advance.

Then, in step S1, the imaging condition setting unit 40 displays a setting screen of image conditions on the display unit 34. An operator inputs information designating various parameters included in imaging conditions to the imaging condition setting unit 40 by referring to the setting screen of imaging conditions and operating the input device 33. Consequently, imaging conditions including an imaging part, an imaging region and a pulse sequence are set in the imaging condition setting unit 40. In a case of imaging fluid having periodicity such as blood flow, data acquisition timing such as ECG synchronization is set as an imaging condition.

In addition, application conditions such as kinds, the number, application regions, an application order and application timings of RF pre-pulses for adjusting a contrast are set as a part of imaging conditions by the pre-pulse setting part 40A in accordance with information input from the input device 33. Application regions of RF pre-pulses can be set on locator image data displayed on the display unit 34.

Nest, in step S2, the contrast verification information generating part 40B generates image information for verifying an image contrast obtained by applying the RF pre-pulses visually by the operator in accordance with the application conditions of RF pre-pulses set in the pre-pulse setting part 40A. Then, the contrast verification information generating part 40B displays the generated image information as contrast verification image information on the setting screen of imaging conditions.

The contrast verification image data can be generated according to the number of applications, application regions and TIs of IR pulses and Presat pulses. When a single IR pulse is applied, the longitudinal magnetization vector, in the application region, produced by applying a static magnetic field is inverted. When a single Presat pulse is applied, an absolute value of the longitudinal magnetization in the application region becomes zero. Then, the longitudinal magnetization is recovered by the longitudinal (T1) relaxation as time passes from an application timing of a RF pre-pulse. A period from an application timing of an IR pulse to an acquisition timing of NMR signals is called T1.

If NMR signals used for generating image data are not absolute values of complex signals but real signals each possibly having a plus or minus value, a region in which the longitudinal magnetization has a plus value is depicted as a high signal part and a region in which the longitudinal magnetization has a minus value is depicted as a low signal part. In case of a brightness display with a gray scale, a high signal part is to be displayed in white and a low signal part is to be displayed in black.

Therefore, in a region in which an IR pulse is applied an even number of times, the longitudinal magnetization has a plus value and is to be depicted as a white high signal region. In contrast, in a region in which an IR pulse is applied an odd number of times, the longitudinal magnetization has a minus value and is to be depicted as a black low signal region.

Accordingly, image data which displays schematically a region where an IR pulse is applied an even number of times in white and a region where an IR pulse is applied an odd number of times in black respectively can be generated as contrast verification image data. Of course, image data showing visually identified high signal regions and low signal regions in locator image data for setting an application region of an IR pulse may be generated as the contrast verification image data. The generated contrast verification image can be displayed on the setting screen of imaging conditions on the display unit 34 in real time.

Figure 4:
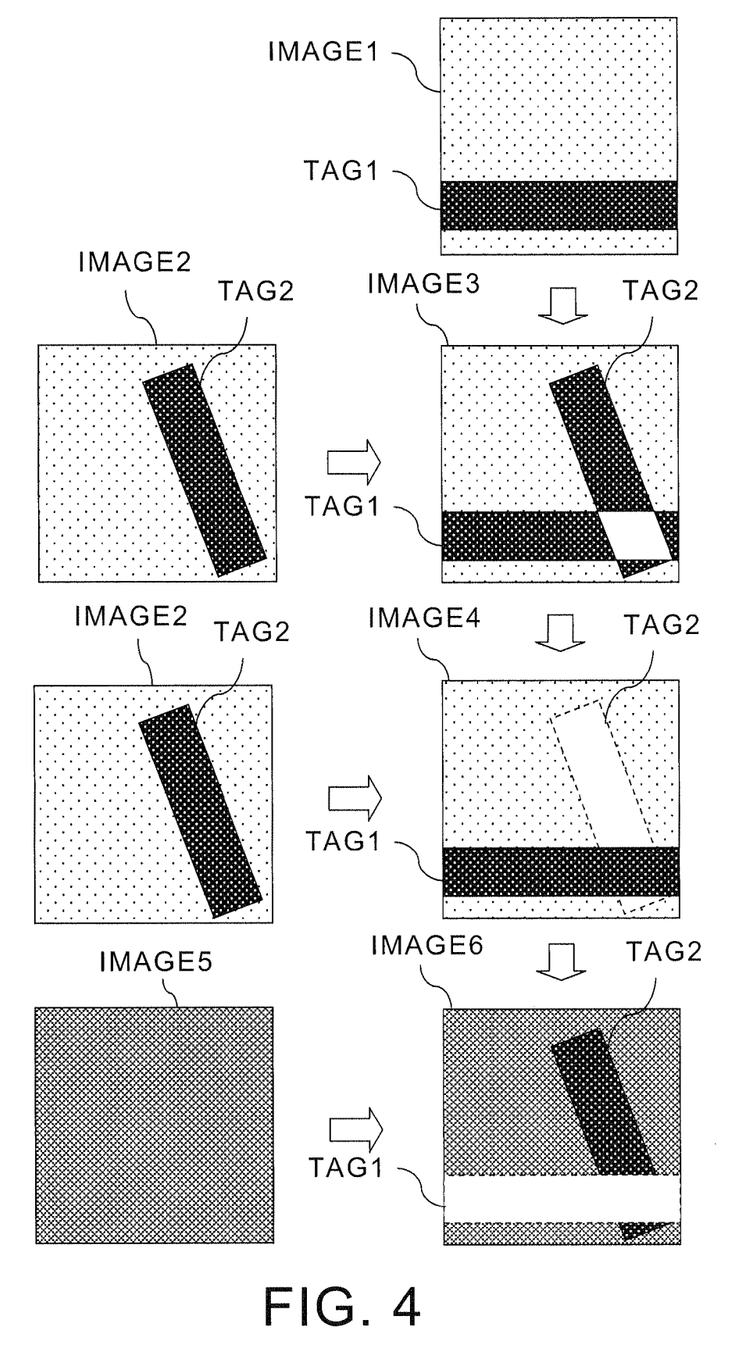
FIG. 4 is a view showing an example of image information for contrast verification generated in the contrast verification information generating part shown in FIG. 1.

FIG. 4 is a view showing an example of image information for contrast verification generated in the contrast verification information generating part 40B shown in FIG. 1.

For example, when the first region selective IR pulse of which application region is a rectangular spatial region shown by TAG1 within an imaging region is set first, a contrast verification image as shown by IMAGE1 is displayed. That is, a single IR pulse is applied in the application region TAG1 of the first region selective IR pulse. On the other hand, IR pulses are not applied in the other region. Therefore, the contrast verification image is displayed so that the application region TAG1 of the first region selective IR pulse is displayed with black or dark gray and the other region is displayed with white or light gray.

Next, when the second region selective IR pulse of which application region is a rectangular spatial region shown by TAG2 is set, a contrast verification image as shown by IMAGE2 is displayed similarly to IMAGE1. The application region TAG2 of the second region selective IR pulse is different from the application region TAG1 of the first region selective IR pulse and is a rectangular region overlapping with the application region TAG1 of the first region selective IR pulse.

Furthermore, when applications of the second and the first region selective IR pulses are combined, the contrast verification image as shown by IMAGE3 is displayed. That is, a single IR pulse is applied to the region, in which the application regions TAG1 and TAG2 of the first and the second region selective IR pulses are not overlapped mutually, out of the application regions TAG1 and TAG2 of the first and the second region selective IR pulses. On the other hand, an IR pulse is applied twice to the region in which the application regions TAG1 and TAG2 of the first and the second region selective IR pulses are overlapped mutually.

Therefore, the contrast verification image is displayed so that the application regions TAG1 and TAG2 of the first and the second region selective IR pulses not overlapped mutually are displayed with black or dark gray and the other regions including the overlapping region of the application regions TAG1 and TAG2 of the first and the second region selective IR pulses are displayed with white or light gray.

Next, when the third region selective IR pulse is set to the application region TAG2 which is same as the application region of the second region selective IR pulse, the contrast verification image as shown by IMAGE4 is displayed. Subsequently, when the third region selective IR pulse is set so as to be combined with the first and the second region selective IR pulses, the setting corresponds to adding the labeling effect as shown by IMAGE2 to that as shown by IMAGE3 visually.

In this case, only the first region selective IR pulse is applied once to the region, out of the application region TAG1 of the first region selective IR pulse, without overlapping with the application region TAG2. On the other hand, an IR pulse is applied twice to the region, out of the application region TAG2 of the second and third region selective IR pulses, without overlapping with the application region TAG1. Further, an IR pulse is applied third time to the overlapping region of the application regions TAG1 and TAG2 of the first, second and third region selective IR pulses. That is, an IR pulse is applied once or three times to the application region TAG1 of the first region selective IR pulse while an IR pulse is not applied or applied twice to the other regions.

Therefore, the contrast verification image is displayed so that the application region TAG1 of the first region selective IR pulse is displayed with black or with dark gray and the other regions including the application region TAG2 of the second and the third region selective IR pulses are displayed with white or with light gray.

Note that, in an example shown in FIG. 4, the contrast verification image is color-coded by white or light gray so that the region to which an IR pulse is applied twice and the region to which no IR pulse is applied are visually distinguished. That is, the region, out of the application region TAG2 of the second and third region selective IR pulses, which is not overlapped with the application region TAG1 is displayed with white since an IR pulse is applied twice and the region to which no region selective IR pulse is applied is displayed with light gray.

Next, when application of a region non-selective IR pulse is set, the contrast verification image as shown by IMAGE6 is displayed. Subsequently, when the region non-selective IR pulse is set to be combined with the first to the third region selective IR pulses, the setting corresponds to adding the labeling effect as shown by IMAGE5 to the labeling effect as shown by IMAGE4.

In this case, the number of applications of an IR pulse increases one time in all regions and the longitudinal magnetization in the data acquisition period is inverted. Therefore, the image obtained by inverting brightness of the contrast verification image shown by IMAGE5 becomes the contrast verification image shown by IMAGE6.

However, in the example shown in FIG. 4, the region to which the only region non-selective IR pulse is applied and the region to which both the region selective and region non selective IR pulses are applied an odd number of times in total are color-coded by density so as to be visually distinguished. That is, the region to which both the region selective and region non selective IR pulses are applied the odd number of times in total is being displayed with dark gray and the region to which the only region non-selective IR pulse is applied is being displayed with slight light gray.

Note that, FIG. 4 shows an example to update a contrast verification image in accordance with a setting order of IR pulses and a setting order of IR pulses does not necessarily correspond to an application order of the set IR pulses. That is, an IR pulse to be applied temporally prior to a previously set IR pulse can be set subsequent to the previously set IR pulse.

Further, FIG. 4 shows an example of the case to apply an IR pulse as an RF pre-pulse. However, in a case of applying a Presat pulse, an application region can be also schematically displayed as a region from which signals are reduced on a contrast verification image. In this case, intensity of signals can be also displayed by a gray scale, as needed.

In case of imaging fluid such as blood flow or CSF, fluid can be selectively depicted so as to be distinguished from a background tissue by wash-in of the fluid into an application region of a region selective IR pulse or wash-out of the fluid from an application region of a region selective IR pulse. Accordingly, an imaginary flow of fluid may be displayed with an estimated contrast in a contrast verification image.

Figure 5:
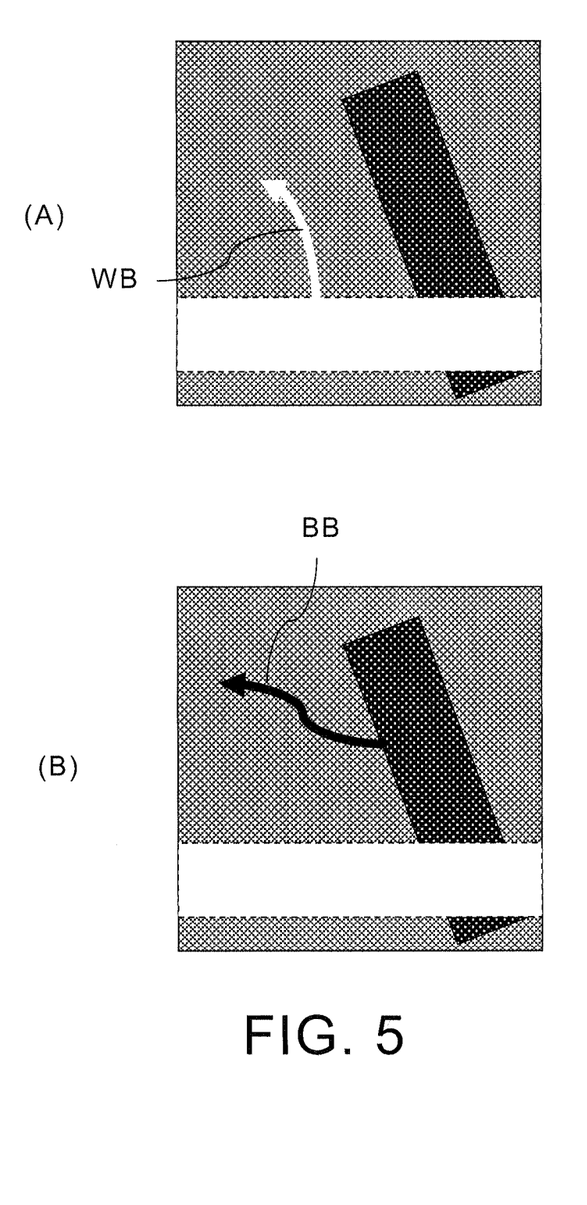
FIG. 5 is a view showing an example of displaying a simulated contrast of blood flow on the contrast verification image shown in FIG. 4.

FIG. 5 is a view showing an example of displaying a simulated contrast of blood flow on the contrast verification image shown in FIG. 4.

FIG. 5 (A) shows a contrast verification image to show schematically that blood flow is depicted as a WB (white blood) image. When blood labeled in a high signal region flows into a low signal region, a background tissue is depicted with black while the labeled blood is depicted with white as shown in FIG. 5 (A). This allows a blood flow image having a satisfactory contrast difference between blood flow signals and background signals to be obtained.

On the other hand, FIG. 5 (B) is a contrast verification image to show schematically that blood flow is depicted as a BB (black blood) image. When blood labeled in a low signal region flows out from a labeling region, blood can be depicted with black as shown in FIG. 5 (B). Note that, if an outflow destination of blood is a high signal region, a satisfactory contrast difference can be obtained since a background tissue is depicted with white while the blood is depicted with black.

Therefore, whether blood is depicted as WB or BB depends on a labeling region and a direction of blood flow. When a flow of fluid is displayed on a contrast verification image, the contrast verification information generating part 40B generates contrast verification image data to display WB image data or BB image data as a simulation based on a labeling region, outline information of blood vessels, a direction of blood flow and the number of applications of an IR pulse.

In this case, the contrast verification information generating part 40B extracts a contour of a blood vessel passing through a border of a labeling region from previously acquired arbitrary image data such as locator image data firstly. Outline extraction processing of a blood vessel can be performed by image processing including known processing such as threshold processing to pixel values and edge extraction processing.

Especially, in the case of imaging blood flow, an artery is often imaged. An artery can be selectively depicted by subtraction processing between frames of image data corresponding to a cardiac diastole and a cardiac systole respectively. Accordingly, an outline of an artery can be extracted clearer by using subtraction image data of frames of image data corresponding to a diastole and a systole respectively.

Next, the contrast verification information generating part 40B automatically determines a direction of blood flow in a blood vessel passing through a border of a labeling region in accordance with arbitrary criteria such as a criterion based on anatomy information or an experimental criterion. Note that, an operator may designate a blood vessel to be a target for determination in a direction of blood flow by operating the input device 33 in advance.

Then, the contrast verification information generating part 40B generates a contrast verification image data as a simulation so that blood vessels in which blood flows from a labeling region to be a high signal region toward a low signal region of the outside and blood inflows from the outside to be a high signal region to the labeling region to be a low signal region are displayed as WB regions. The contrast verification information generating part 40B also generates the contrast verification image data so that blood vessels in which blood flows from the labeling region to be a low signal region toward a high signal region of the outside and blood inflows from the outside to be a low signal region to the labeling region to be the high signal region are displayed as BB regions.

The generated contrast verification image data is displayed on the display unit 34. Then, the operator can grasp the blood vessels depicted as WB and BB respectively on the contrast verification image.

As described above, determining a direction of blood flow in a blood vessel traveling through a border of an application region of a RF pre-pulse makes it possible to generate a contrast verification image showing whether blood is depicted with white or with black based on the direction of the blood flow.

Note that, an operator may designate a direction of blood flow for each blood vessel manually by operating the input device 33 and also modify a direction of blood flow determined automatically as a default by operating the input device 33.

In the examples shown in FIG. 4 and FIG. 5, the cases to display a contrast verification image easily based on the number of applications and application regions of IR pulses without considering an application order of IR pulses and T1 relaxation have been described. However, a contrast verification image to show an influence of T1 relaxation according to respective application timings of RF pre-pulses such as an IR pulse and a Presat pulse based on the respective application timings may be generated.

That is, signal intensities in an application region of an IR pulse vary depending on a TI. Similarly, a period from an application timing of a Presat pulse to a data acquisition timing also influences signal intensities from the application region of the Presat pulse. Accordingly, a contrast verification image to schematically show indexes of relative signal intensities according to periods from a TI and an application timing of a Presat pulse to a data acquisition timing can be also generated.

For example, a contrast verification image to display a rate in relative signal intensity, that a region showing the lowest signal is 0% while a region showing the highest signal is 100%, for each region can be generated. The rates in signal intensity can be shown with a gray scale according to the rates. Alternatively, a rate itself in signal intensity may be displayed as a numerical value on a contrast verification image. That is, a normalized map of relative signal intensities in which the minimum value is 0% and the maximum value is 100% can be generated as a contrast verification image.

Figure 6:
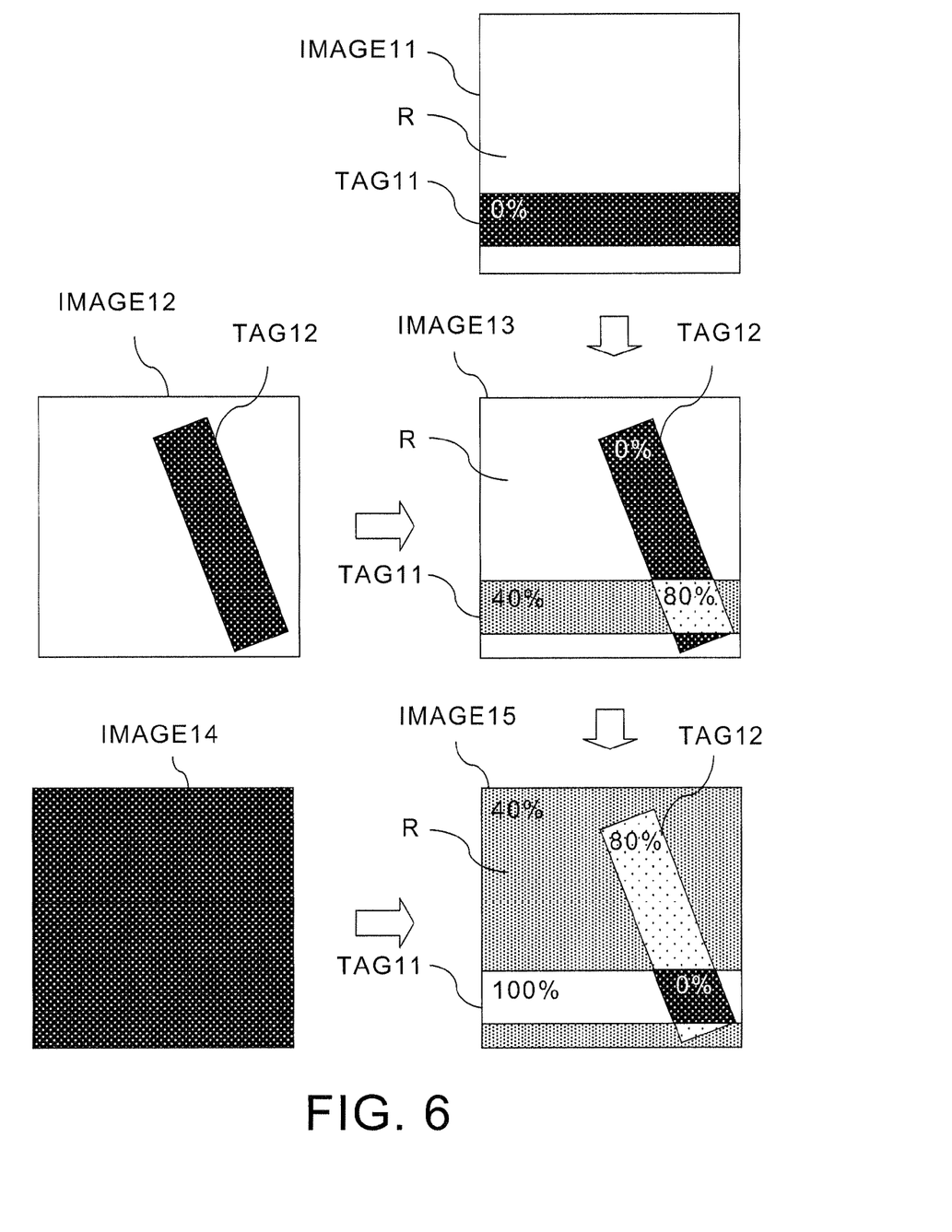
FIG. 6 is a view showing an example of generating image information for contrast verification according to lengths of TIs in the contrast verification information generating part shown in FIG. 1.
Figure 7:
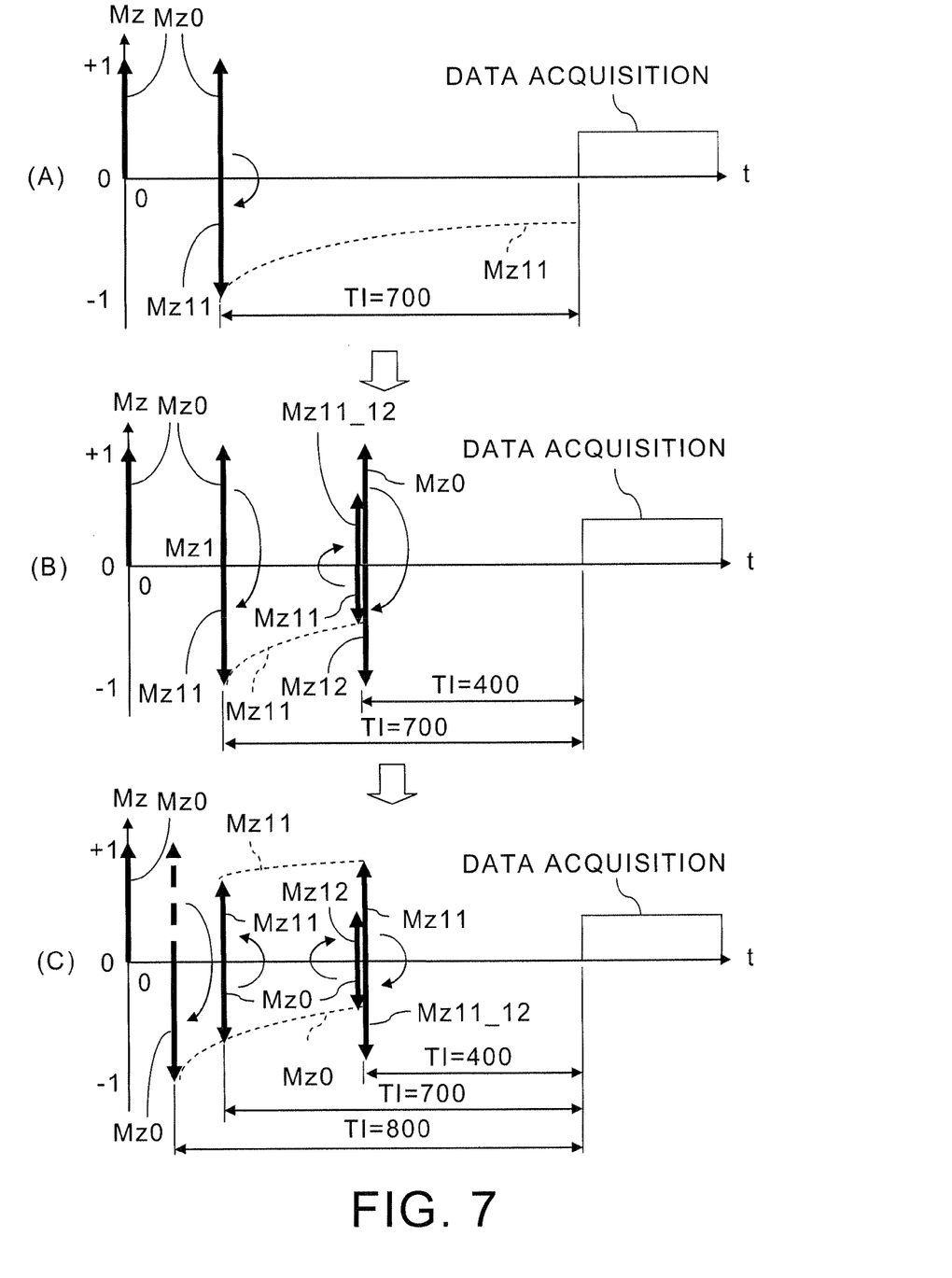
FIG. 7 shows graphs showing time change in the longitudinal magnetization by applying the IR pulses shown in FIG. 6.

FIG. 6 is a view showing an example of generating image information for contrast verification according to lengths of TIs in the contrast verification information generating part 40B shown in FIG. 1. FIG. 7 shows graphs showing time change in the longitudinal magnetization by applying the IR pulses shown in FIG. 6.

In FIGS. 7 (A), (B) and (C), the respective horizontal axes show time t and the respective vertical axes show normalized longitudinal magnetization Mz. As shown in FIG. 7 (A), at an initial state t=0 before applying an IR pulse, the longitudinal magnetization Mz0 in an imaging region R becomes a positive maximum value +1 by influence of a static magnetic field.

Subsequently, to the application region TAG11 shown in FIG. 6, an application of the first region selective IR pulse set as TI=700 is set for example. Then, the longitudinal magnetization Mz11 in the application region TAG11 of the first region selective IR pulse is inverted from the maximum value +1 to the negative minimum value −1 at the timing corresponding to TI=700 from a data acquisition period as shown in FIG. 7 (A). On the other hand, the longitudinal magnetization Mz0 in the other imaging region R remains the positive maximum value +1.

Therefore, signals having the minimum intensities are generated from the application region TAG11 immediately following the application of the first region selective IR pulse while signals having the maximum intensities are generated from the other imaging region R. That is, a contrast difference between the internal and the external of the application region TAG11 immediately following the application of the first region selective IR pulse becomes the maximum.

Therefore, IMAGE11 in which the internal of the application region TAG11 of the first region selective IR pulse is displayed in black and the imaging region R outside the application region TAG11 of the first region selective IR pulse is displayed in white is generated as a contrast verification image as shown in FIG. 6. Further, on the application region TAG11 of the first region selective IR pulse, 0% is displayed.

As shown with the dotted line in FIG. 7 (A), the longitudinal magnetization Mz11 in the application region TAG11 of the first region selective IR pulse is recovered gradually by T1 relaxation after immediately following the application of the first region selective IR pulse.

Next, as shown in FIG. 6, an application of the second region selective IR pulse set as TI=400 is set to the application region TAG12 which is different from and overlaps with the application region TAG11 of the first region selective IR pulse. This setting corresponds visually to adding the labeling effect shown by the contrast verification image IMAGE12 after the labeling effect shown by the contrast verification image IMAGE11 receives an influence by T1 relaxation.

Then, as shown in FIG. 7 (B), the longitudinal magnetization Mz12 in the application region TAG12 of the second region selective IR pulse which does not overlap with the application region TAG11 of the first region selective IR pulse is inverted from the maximum value +1 to a negative value at the timing corresponding to TI=400. On the other hand, the longitudinal magnetization Mz0 of the other imaging region R in which neither the first nor the second region selective IR pulse is applied remains the positive maximum value +1.

Further, the longitudinal magnetization Mz11_12 in the application region TAG12 of the second region selective IR pulse which overlaps with the application region TAG11 of the first region selective IR pulse becomes the value derived by inverting the longitudinal magnetization Mz11, in the application region TAG11 of the first region selective IR pulse, recovered by the T1 relaxation in the period from TI=700 to TI=400. On the other hand, the longitudinal magnetization Mz11, in the application region TAG11 of the first region selective IR pulse which does not overlap with the application region TAG12 of the second region selective IR pulse, i.e., the application region TAG11 to which only the first region selective IR pulse is applied, remains the value recovered by the T1 relaxation in the period from TI=700 to TI=400.

Note that, in FIG. 7 (B), the vectors representing the longitudinal magnetizations Mz0, Mz11, Mz12 and Mz11_12 in the respective regions are mutually overlapped practically at the timing TI=400. However, the vectors are displayed without overlapping for description.

Immediately following the application of the second region selective IR pulse, the signals showing the minimum intensities are generated from the application region TAG12 in which only the second region selective IR pulse is applied. Meanwhile, the signals having maximum intensities are generated from the imaging region R in which neither the first nor the second region selective IR pulse is applied. The signals having relative low intensities are generated from the application region TAG11 in which only the first region selective IR pulse is applied while the signals having relative high intensities are generated from the overlapped region of the application regions TAG11 and TAG12 in which both the first and the second region selective IR pulses are applied.

Therefore, IMAGE13 is generated as the contrast verification image as shown in FIG. 6. The IMAGE13 displays the inside of the application region TAG12 in which only the second region selective IR pulse is applied with black, the imaging region R in which neither the first nor the second region selective IR pulse is applied with white, the inside of the application region TAG11 in which only the first region selective IR pulse is applied with dark gray and the overlapped region of the application regions TAG11 and TAG12 in which both the first and the second region selective IR pulses are applied with light gray respectively.

In addition, each rate in relative signal intensity is displayed as a numerical value. Specifically, 0% is displayed on the application region TAG12 in which only the second region selective IR pulse is applied. 40% is displayed on the application region TAG11 in which only the first region selective IR pulse is applied. 80% is displayed on the overlapped region of the application regions TAG11 and TAG12 in which both the first and the second region selective IR pulses are applied.

Next, an application of region non-selective IR pulse is set at the timing to be TI=800 before the applications of the first and the second region selective IR pulses. This setting corresponds visually to adding the labeling effect shown by the contrast verification image IMAGE14 prior to the labeling effect shown by the contrast verification image IMAGE13.

Then, the longitudinal magnetization Mz0 of all imaging regions R is inverted from the maximum value +1 to the negative minimum value −1 immediately following the application of the region non-selective IR pulse as shown in FIG. 7 (C). Further, the longitudinal magnetization Mz11 in the application region TAG11 of the first region selective IR pulse becomes the value, into which the longitudinal magnetization Mz0 of the imaging region R recovered by the T1 relaxation during the period from TI=800 to TI=700 is inverted, immediately following the application of the first region selective IR pulse. On the other hand, the longitudinal magnetization Mz0 of the other imaging region R remains the value recovered by the T1 relaxation during the period from TI=800 to TI=700.

Further, the longitudinal magnetization Mz12, in the application region TAG12 to which only the second region selective IR pulse is applied, becomes an inverted value of the longitudinal magnetization Mz0 of the imaging region R, to which neither the first nor the second region selective IR pulse is applied, by recovery due to the T1 relaxation during the period from TI=800 to TI=400 immediately following the application of the second region selective IR pulse. Meanwhile, the longitudinal magnetization Mz0 of the imaging region R, to which neither the first nor the second region selective IR pulse is applied, remains the value recovered by the T1 relaxation during the period from TI=800 to TI=400.

Further, the longitudinal magnetization Mz11 in the application region TAG11, to which only the first region selective IR pulse is applied, immediately following the application of the second region selective IR pulse becomes the value recovered by the T1 relaxation during the period from TI=700 to TI=400. Meanwhile, the longitudinal magnetization Mz11_12 in the overlapped region of the application regions TAG11 and TAG12, to which both the first and the second region selective IR pulses are applied, becomes the value derived by inverting the longitudinal magnetization Mz11, in the application region TAG11 of the first region selective IR pulse, recovered by the T1 relaxation during the period from TI=700 to TI=400.

Consequently, in an example shown in FIG. 7 (C), signals having the maximum intensities are generated from the application region TAG11 to which only the region non selective IR pulse and the first region selective IR pulse are applied in the data acquisition period while signals having the minimum intensities are generated from the overlapped region of the application regions TAG11 and TAG12 to which all of the first and the second region selective IR pulses and the region non-selective IR pulses are applied. Further, signals having relative low intensities are generated from the imaging region R to which only the region non-selective IR pulse is applied while signals having relative high intensities are generated from the application region TAG12 to which only the region non selective IR pulse and the second region selective IR pulse are applied.

Therefore, IMAGE15 as shown in FIG. 6 is generated as a contrast verification image. Specifically, in the IMAGE15, the internal of the application region TAG11, to which the only region non-selective IR pulse and the first region selective IR pulse are applied, is displayed with white. The overlapped region of the application regions TAG11 and TAG12, to which all of the first and the second region selective IR pulses and the region non-selective IR pulses are applied, is displayed with black. The internal of the application region TAG12, to which only the region non-selective IR pulse and the second region selective IR pulse are applied, is displayed with light gray. The imaging region R, to which only the region non-selective IR pulse is applied is displayed with dark gray.

In addition, each rate in relative signal intensity is displayed as a numerical value. Specifically, the application region TAG11 of only the region non-selective IR pulse and the first region selective IR pulse is 100%. The application region TAG12 of only the region non-selective IR pulse and the second region selective IR pulse is 80%. The imaging region R, to which only the region non-selective IR pulse is applied, is 40%. The overlapped region of the application regions TAG11 and TAG12, to which all of the first and the second region selective IR pulses and the region non-selective IR pulses are applied, is 0%.

As described above, a contrast verification image to be displayed as a simulation with a gray scale and/or numerical values can be generated so as to verify visually relative signal intensities with considering the T1 relaxation in each region depending on TIs. The numerical values to show relative signal intensities may be values of normalized longitudinal magnetizations or values of signal intensities themselves as well as rates as shown in FIG. 7.

Note that, in case of generating an image, which shows information for verifying contrast on a reference image such as a locator image, as a contrast verification image, the information for verifying the contrast can be displayed in various ways. Easy examples include a method for displaying border lines of application regions of region selective RF pre-pulses with a gray scale corresponding to a contrast. Alternatively, an arbitrary one or two out of R (red) signals, G (green) signals and B (blue) signals for displaying a reference image generated with a gray scale may be modulated according to an estimated contrast to display the reference image.

The time constant of T1 relaxation (T1 value) is known as a unique value for each matter. Therefore, a relative signal intensity in each region can be obtained based on a TI and a T1 value. In practical imaging, signals from a desired tissue such as blood are selectively enhanced or suppressed by adjusting each TI with using a difference in T1 relaxation time between tissues like blood and a background tissue. Accordingly, for generating a contrast verification image, a relative signal intensity in each region can be approximately estimated using a T1 value corresponding to a main component such as a background tissue consisting of each region or a representative value such as a weighted average of T1 values.

When a T1 value according to a matter in each region is used, an image showing an influence of T1 relaxation according to the T1 value varying depending on a matter is generated as a contrast verification image. Therefore, is becomes necessary to specify T1 values corresponding to respective regions.

The T1 value becomes variable having a parameter as information specifying a matter. That is, T1 values can be related with names of matters including a WM (white matter) of cerebrum, a GM (gray matter) of cerebrum, fat, a myocardium, a prostate and a liver in advance. Further, so long as an imaging part and/or an application part of a region selective RF pre-pulse, such as a head part, an abdomen part or a breast part, is specified, a major matter consisting of the part can be specified. Therefore, parts can be also related with T1 values.

Accordingly, at least one of a matter, a T1 value and a part corresponding to an imaging region or an application region of a region selective RF pre-pulse can be designated manually by an operator. For a concrete example, a matter or a part to be labeled and a matter or a part in an imaging region can be selected from choices such as a pull-down menu by operation of the input device 33. Alternatively, representing values of T1 values corresponding to application regions of region selective RF pre-pulses and an imaging region may be directly input as numerical values by operation of the input device 33

Then, the contrast verification information generating part 40B can acquire information designating matters from the input device 33 to generate an image showing an influence of the T1 relaxation based on at least one of the T1 values of the designated matters, the designated T1 values and the T1 values of matters corresponding to the designated parts.

Meanwhile, a T1 value corresponding to at least one of an application region of a region selective RF pre-pulse and an imaging region may be automatically set or indicated. For example, when an application region of a region selective RF pre-pulse has been manually set by operation of the input device 33, the purpose is considered to label a fluid such as blood ordinarily. Accordingly, a T1 value in an application region of a region selective RF pre-pulse set by operation of the input device 33 can be automatically set to a T1 value of blood or CSF.

On the other hand, a T1 value in a region other than an application region of a region selective RF pre-pulse set by operation of the input device 33 can be automatically set to a T1 value of a background tissue. However, a background tissue has possibilities according to imaging parts including a GM and a myocardium. Therefore, a background tissue may be selected from choices.

Further, in case of using a reference image, such as a locator image, for generating a contrast verification image, regions can be extracted by outline extraction processing, such as edge extraction processing, of the reference image. Accordingly, an image showing an influence of the T1 relaxation can be generated based on T1 values of matters corresponding to extracted regions. In this case, anatomical information may be referred to for specifying a matter or a part in a region extracted by outline extraction processing. Specifically, a matter or a part in each region can be specified by pattern matching with anatomical information, analytic processing or the like.

By the way, FIG. 4, FIG. 5, and FIG. 6 show the example to set labeling regions by RF pre-pulses inside an imaging region. However, labeling regions by RF pre-pulses may be set outside an imaging region. In this case, fluid such as blood labeled outside an imaging region is depicted by flowing into the imaging region.

Figure 8:
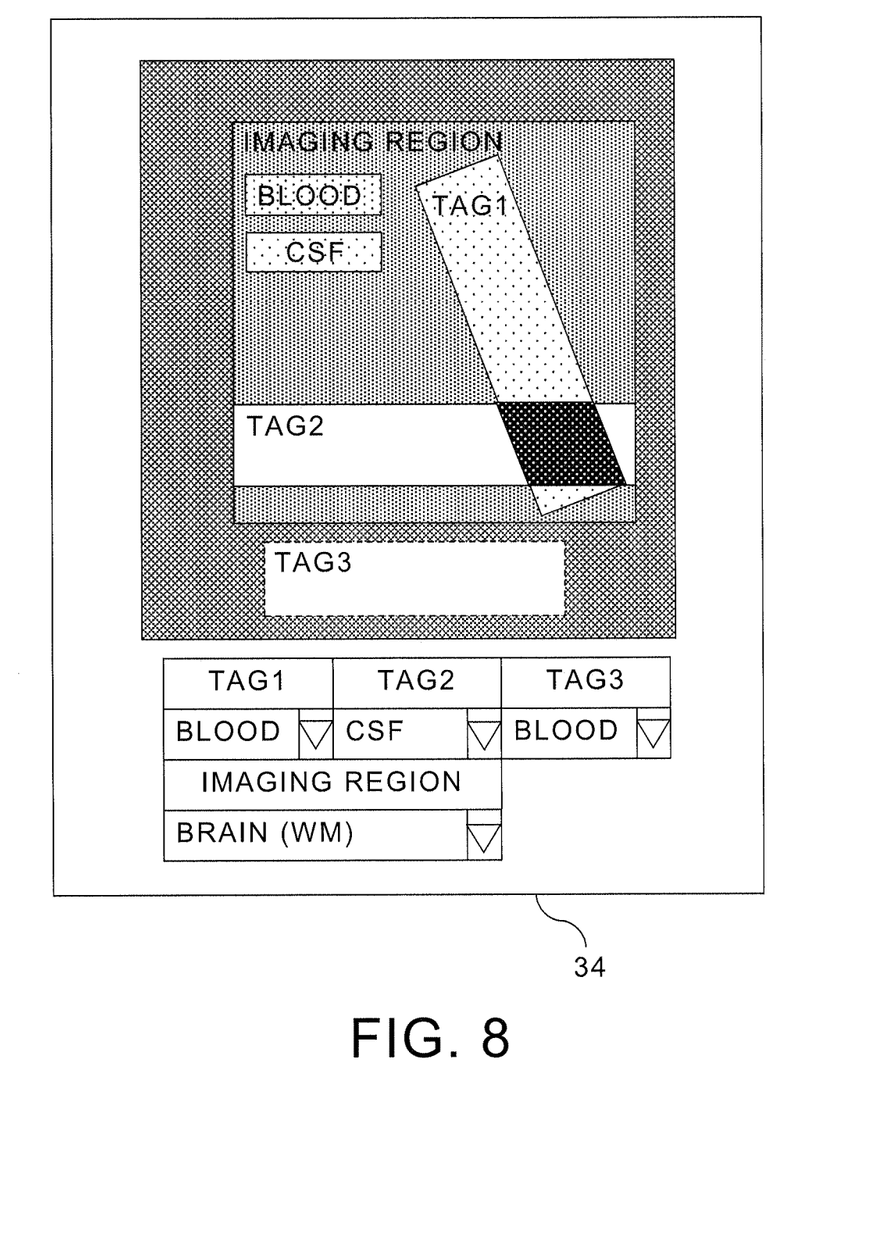
FIG. 8 is a view showing an example of image information, including a region outside of an imaging region, for verifying contrast made by the contrast verification information generating part show in FIG. 1.

FIG. 8 is a view showing an example of image information, including a region outside of an imaging region, for verifying contrast made by the contrast verification information generating part 40B show in FIG. 1.

As shown in FIG. 8, image information for verifying a contrast can be made as an image by which at least one of an application region of a region selective RF pre-pulse set outside of an imaging region and that set as a same region as the imaging region can be verified. In the example shown in FIG. 8, it can be seen that an application region of a region selective RF pre-pulse identified by TAG3 is set outside of an imaging region.

Further, matters can be designated for application regions of region selective RF pre-pulses and an imaging region as an example of pull-down menus, displayed below the contrast verification image, shown in FIG. 8. Consequently, a contrast verification image having a contrast according to TIs and T1 values of respective regions can be generated and displayed.

Furthermore, a luminance based on a T1 value of a fluid such as blood or CSF may be displayed schematically with a gray scale on an arbitrary position such as inside of an imaging region. In the example shown in FIG. 8, luminances based on T1 values of fluids are displayed on the imaging region other than each application region of region selective RF pre-pulses set by operation of the input device 33. Hence, an operator can compare a luminance based on a T1 value of a fluid with that corresponding to an imaging region other than each application region of region selective RF pre-pulses set by operation of the input device 33.

Next, in step S3 of FIG. 3, the imaging condition setting unit 40 becomes a standby condition for inputting a starting instruction of an imaging scan from the input device 33. An operator can reset imaging conditions including application conditions of RF pre-pulses with referring to a contrast verification image displayed on a setting screen of imaging conditions.

In the case described above, in step S3, it is determined that information instructing for starting of a scan has not been input by the imaging condition setting unit 40. Then, in step S1, resetting imaging conditions including application conditions of RF pre-pulses is performed again by the imaging condition setting unit 40.

To the contrary, when an operator determines that resetting imaging conditions including application conditions of RF pre-pulses is unnecessary, information instructing for starting of a scan is input from the input device 33 to the imaging condition setting unit 40. Therefore, in step S3, it is determined that information instructing for starting of a scan has been input by the imaging condition setting unit 40.

In this case, in step S4, a MR imaging scan is performed in accordance with the imaging conditions including the application conditions of the RF pre-pulses set in the imaging condition setting unit 40.

That is, the imaging conditions including a pulse sequence is output from the imaging condition setting unit 40 to the sequence controller 31. The sequence controller 31 generates gradient magnetic fields in the imaging region having a set object P by driving the gradient power supply 27, the transmitter 29 and the receiver 30 according to the pulse sequence and generates RF signals including RF pre-pulses and RF excitation pulses from the RF coil 24.

Therefore, NMR signals generated by nuclear magnetic resonance inside the object P are received by the RF coil 24 to be provided to the receiver 30. The receiver 30 generates raw data, which is digitized data of NMR signals, by A/D conversion after receiving the NMR signals from the RF coil 24 and performing predetermined signal processing. The receiver 30 gives the NMR signals to the sequence controller 31. The sequence controller 31 outputs the NMR signals to the computer 32.

Then, the data processing unit 41 obtains the NMR signals from the sequence controller 31 and arranges the NMR signals as k-space data in k-space formed in the k-space data storage unit 42.

In MRA, the acquisition and arrangement of k-space data described above are often performed in synchronized with an ECG signal. In this case, an ECG signal obtained by the ECG unit 38 is output to the sequence controller 31 to be used as a synchronization signal.

Note that, the k-space data is acquired as NMR signals of which signal intensities from specific objects such as blood flow in target blood vessels are enhanced or suppressed by RF pre-pulses such as a region selective IR pulse and a region non-selective IR pulse.

Next, in step S5, image data is generated based on the k-space data acquired by the imaging scan. That is, the data processing unit 41 reconstructs image data by retrieving the k-space data from the k-space data storage unit 42 and performing image reconstruction processing. Then, the generated image data is displayed on the display unit 34 after performing required image processing of the image data.

Consequently, a MR image such as a blood flow image having a contrast verified in advance through the contrast verification image on the setting screen of imaging conditions is displayed on the display unit 34. Subsequently, the image data is stored in the image data storage unit 43 as needed.

That is, the magnetic resonance imaging apparatus 20 described above is the apparatus configured to display a contrast verification image for verifying an image contrast based on application conditions such as application regions and the number of applications of plural RF pre-pulses including a region selective RF pulse in order to obtain a desired contrast in a case of setting imaging conditions with applications of the RF pre-pulses.

Therefore, by the magnetic resonance imaging apparatus 20, it can be verified in advance whether a region of interest (ROI) is depicted darkly as a low signal region or in white as a high signal region. Consequently, it becomes possible to set imaging conditions including an application region of a RF pre-pulse easily and appropriately. Especially, it is efficient for MRA in which setting application regions of RF pre-pulses according to a traveling direction of a blood vessel is significant.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
    an imaging condition setting unit configured to set an imaging condition for applying radio frequency pre-pulses to adjust a contrast, the radio frequency pre-pulses including a region selective radio frequency pulse;
    a verification image generating unit configured to generate and display an image for verifying the contrast based on application conditions including an application region and an application number of the radio frequency pre-pulses; and
    an imaging unit configured to perform magnetic resonance imaging according to the imaging condition.

2. A magnetic resonance imaging apparatus of claim 1, wherein said verification image generating unit is configured to generate an image representing an influence of a longitudinal relaxation according to respective application timings of the radio frequency pre-pulses based on the respective application timings.

3. A magnetic resonance imaging apparatus of claim 1, wherein said verification image generating unit is configured to generate an image showing a flow of a fluid with an estimated contrast as the image for verifying the contrast.

4. A magnetic resonance imaging apparatus of claim 3, wherein said verification image generating unit is configured to determine a direction of blood flow in a blood vessel passing through a border of an application region of a radio frequency pre-pulse to generate an image representing whether blood is depicted with white or with black based on the direction.

5. A magnetic resonance imaging apparatus of claim 1, wherein said imaging condition setting unit is configured to set a labeling pulse for labeling fluid flowing in an object as at least one of the radio frequency pre-pulses.

6. A magnetic resonance imaging apparatus of claim 5, wherein said imaging condition setting unit is configured to set a region selective inversion recovery pulse as the labeling pulse.

7. A magnetic resonance imaging apparatus of claim 2, wherein said verification image generating unit is configured to generate an image representing an influence of a longitudinal relaxation according to a value of a longitudinal relaxation time showing a different value for each matter as the image for verifying the contrast.

8. A magnetic resonance imaging apparatus of claim 7, further comprising:
    a matter designating unit configured to designate at least one of matter, a T1 value and a part corresponding to an application region of a region selective radio frequency pre-pulse,
    wherein said verification image generating unit is configured to generate the image representing the influence of the longitudinal relaxation based on at least one of a T1 value of the designated matter, the designated T1 value and a T1 value of a matter corresponding to the designated part.

9. A magnetic resonance imaging apparatus of claim 7, wherein said verification image generating unit is configured to generate the image representing the influence of the longitudinal relaxation with setting a T1 value of blood to a T1 value of an application region of a region selective radio frequency pre-pulse set by operation of an input device.

10. A magnetic resonance imaging apparatus of claim 7, wherein said verification image generating unit is configured to generate the image representing the influence of the longitudinal relaxation with setting a T1 value of a background tissue to a T1 value of a region other than an application region of a region selective radio frequency pre-pulse set by operation of an input device.

11. A magnetic resonance imaging apparatus of claim 7, wherein said verification image generating unit is configured to display a brightness based on a T1 value of a fluid so as to be compared with a brightness based on a T1 value corresponding to a region other than an application region of a region selective radio frequency pre-pulse set by operation of an input device.

12. A magnetic resonance imaging apparatus of claim 1, wherein said verification image generating unit is configured to generate an image showing information for verifying a contrast on a reference image of an object as the image for verifying the contrast.

13. A magnetic resonance imaging apparatus of claim 12, wherein said verification image generating unit is configured to generate an image representing an influence of a longitudinal relaxation based on a T1 value of a matter corresponding to a region extracted by outline extraction processing of the reference image.

14. A magnetic resonance imaging apparatus of claim 2, wherein said verification image generating unit is configured to generate the image for verifying the contrast as an image by which at least one of an application region of a region selective radio frequency pre-pulse set outside of an imaging region and an application region of a region selective radio frequency pre-pulse set to a same region as the imaging region can be verified.

15. A magnetic resonance imaging method comprising:
setting an imaging condition for applying radio frequency pre-pulses to adjust a contrast, the radio frequency pre-pulses including a region selective radio frequency pulse;
generating and displaying an image for verifying the contrast based on application conditions including an application region and an application number of the radio frequency pre-pulses; and
performing magnetic resonance imaging according to the imaging condition.

* * * * *